United States Patent [19]

Bohannon

[11] Patent Number: 5,763,158

[45] Date of Patent: Jun. 9, 1998

[54] DETECTION OF MULTIPLE ANTIGENS OR ANTIBODIES

[75] Inventor: Robert C. Bohannon, Dugway, Utah

[73] Assignee: The United States of America as represented by the Secretary of the Army, Washington, D.C.

[21] Appl. No.: 796,772

[22] Filed: Feb. 6, 1997

[51] Int. Cl.$^6$ .................. C12Q 1/001; C12Q 1/54; C12Q 1/02; G01N 33/53

[52] U.S. Cl. .................. 435/4; 435/7.1; 435/12; 435/21; 435/28; 435/14; 435/29; 435/34; 435/235.1; 435/968; 422/50; 422/52; 422/55; 422/68.1

[58] Field of Search .................. 435/4, 7.1, 12, 435/21, 28, 14, 29, 34, 235.1, 968; 422/50, 52, 55, 68.1

[56] References Cited

U.S. PATENT DOCUMENTS

| | | | |
|---|---|---|---|
| 4,459,359 | 7/1984 | Neurath | 435/4 |
| 4,727,019 | 2/1988 | Valkirs et al. | 435/4 |
| 5,518,882 | 5/1996 | Lund et al. | 435/4 |

*Primary Examiner*—Louise Leary
*Attorney, Agent, or Firm*—William R. Medsger

[57] ABSTRACT

A method for simultaneously testing a sample for the presence of multiple target antigens or antibodies in the sample, which comprises presenting the sample to a plurality of different binding sites, wherein at least two of the sites are binding sites for different known target antigens or antibodies, each known binding site is composed of at least one molecule of a ligand-enzyme complex attached to a support, and the ligand-enzyme complex is a ligand attached to an enzyme in proximity to the enzyme's active site such that the enzymatic activity of the ligand-enzyme complex is changed when the target antibody or antigen is present in the sample. The ligand-enzyme complex embraces nonenzymatic reporter molecules such as electrochemiluminescent compounds. The method also includes assaying each binding site for a change in enzymatic or other reporter activity compared to a control value. A device for performing simultaneous detection of multiple target antigens or antibodies is also disclosed.

31 Claims, 4 Drawing Sheets

DETECTION OF MULTIPLE ANTIGENS OR ANTIBODIES

FIELD OF THE INVENTION

The present invention relates generally to immunodiagnostics. More specifically, the present invention relates to the simultaneous detection of multiple antigens or antibodies using a reporter-based assay, such as enzyme-linked immunosorbent assay (ELISA) and electrochemiluminescence.

BACKGROUND OF THE INVENTION

ELISA is a well known technique for detection and measurement of antigens or antibodies in solution which uses enzyme-linked antigens or antibodies to detect an antigen-antibody reaction. This technique has been used in a variety of immunodiagnostic applications such as serodiagnostics to detect antigens from a wide range of specific viruses, bacteria, fungi, and parasites, and to measure the presence of antibodies against these various microorganisms. ELISA is also used to monitor factors involved in noninfectious diseases such as hormone levels, hematological factors, serum tumor markers, drug levels, and antibodies.

Typically, the enzyme used in ELISA is selected from alkaline phosphatase, horseradish peroxidase, and beta-galactosidase and it is coupled to an antibody or antigen. The binding of the enzyme-linked antibody or antigen to its corresponding antigen or antibody is detected by adding substrates that, upon reaction with the enzyme, are converted into colored reaction products or give off luminescence.

An antigen-antibody reaction is traditionally defined as the interaction between an antigenic determinant, or epitope, on the antigen molecule and a corresponding antigen-combining site, or paratope, on the variable region of the antibody molecule. In addition to this interaction, the paratope on the antibody molecule may also serve as an antigenic site, i.e., be recognized by a paratope on the variable region of a second antibody molecule. In this situation, the paratope on the first antibody is referred to as the idiotope. Thus, in its broadest sense, the ELISA technique may be understood as capable of detecting the interaction of specific binding partners, or ligands, which include epitope-paratope interactions and idiotope-paratope interactions.

The type of binding partner interactions which can be detected by ELISA is partially illustrated by a recent description of a modified ELISA technique used to detect the presence of anti-HIV antibody in solution. Brennan et al., in *Protein Engineering* 7(4): 509–514 (1994), describes a modified alkaline phosphatase containing an epitope from the HIV-1 gp120 protein inserted onto its surface in the vicinity of the enzyme's active site. The activity of this modified alkaline phosphatase, which is comparable to the activity of wild type alkaline phosphatase, was reduced by almost half by the binding of an anti-gp120 monoclonal antibody to the gp120 epitope on the modified alkaline phosphatase.

One of the limitations of conventional ELISA methods is that they detect, in a linear or sequential fashion, only one type of antigen or antibody at a time. However, in many situations it would be advantageous to rapidly screen a sample for the presence of multiple antigens or antibodies simultaneously. For example, in the biomedical field, it would be beneficial to have a technique to rapidly determine which pathogen(s) of a number of possibilities has infected a patient so that an appropriate treatment can be implemented without the delay of additional screening. In addition, with the increasing concern about the potential use of biological and chemical weapons by terrorists against civilian populations and by armies in war as weapons of mass destruction, the ability to rapidly detect and identify multiple biological, chemical or toxin agents in the field could improve the ability to treat both civilian populations and military personnel exposed to such agents.

BRIEF DESCRIPTION OF THE INVENTION

Accordingly, an object of the invention is to provide a method, such as an enzyme-linked immunosorbent assay, for simultaneously detecting the presence of multiple antigens or antibodies in a sample.

An additional object of the present invention is to provide a detection device for rapid, simultaneous immunological detection of multiple antigens or antibodies in a sample.

These and other objects are achieved by constructing binding sites specific for different antigens or antibodies; arranging the sites in a manner that allows simultaneous contact of the sites with any antigens or antibodies present in the sample as well as differentiation among the sites; and assaying the sites for binding of antigens or antibodies thereto.

Each binding site is constructed by attaching a ligand, for an antigen or antibody, to an enzyme in the proximity of the active site of the enzyme to create a ligand-enzyme complex. The complex is attached to a support to form a binding site which can be specifically arranged in a known relationship relative to the other binding sites such that an array of binding sites is created. In addition to being attached to the enzyme, the ligand will bind a specific target antigen or antibody present in the sample, or preferably, a monoclonal antibody (mAb) specific for the target antigen or antibody. Upon binding of one of these binding partners to the ligand, the detectable activity of the enzyme portion of the complex is significantly reduced.

The presence of a target antigen or antibody in a sample is detected by assaying for a change in enzymatic activity at the corresponding binding site after its contact with the sample. This change will be a reduction in enzymatic activity if the target antigen or antibody directly binds to the ligand-enzyme complex. Alternatively, when the binding site includes a monoclonal antibody bound to the ligand portion of the complex, the detectable enzymatic activity will be increased due to displacement of the monoclonal antibody from the ligand-enzyme complex by the binding of a competing target antigen or antibody to the monoclonal antibody.

DETAILED DESCRIPTION OF THE INVENTION

As indicated above, the present invention provides rapid, simultaneous detection of multiple antigens or antibodies in a sample using an immunosorbent assay. Antigens or antibodies detectable by the invention are referred to as target molecules and include antigens derived from microorganisms and other pathogens, toxin molecules and other chemical agents such as drugs and nerve agents, and antibodies specific for these pathogens and chemical agents. Target molecules may also be self-antibodies generated in autoimmune diseases. Target antigens include nucleic acids and target antibodies include antibodies against nucleic acids. A target molecule is detected by its interaction with a binding site specific for that target molecule, the binding site comprising a ligand-enzyme complex attached to a support, and preferably, a mAb to the ligand bound to the ligand portion of the complex.

The ligand-enzyme complex is formed by covalently attaching the ligand to an enzyme in the proximity of the active site of the enzyme. The ligand may comprise a small molecule capable of binding to a target antigen or antibody molecule, or a small molecule that is a specific binding partner of an antibody specific for a target antigen or antibody. For example, the ligand may be a peptide (see FIG. 1) which is an epitope of a target antigen, a paratope of a target antibody, a paratope of an antibody specific for a target antigen, or an idiotope of a target antibody. The ligand may also be a nucleic acid molecule, a toxin molecule, a portion thereof, or another chemical agent such as a derivative of a nerve agent or drug. Preferably, the ligand comprises an antigenic site of a target antibody or antigen such that when the ligand is coupled to a carrier and the resulting conjugate is used to immunize mice, a monoclonal antibody (mAb) against the antigenic site on the ligand can be obtained.

Procedures for predicting and determining antigenic sites on target antigens or antibodies are well-known in the art. For example, antigenic sites to proteins of pathogens of interest may be selected using a hydrophobicity computer analysis, e.g., Hopp, T. P. and Woods, K. R., Proc. Natl. Acad. Sci., USA, 78, 3824–8 (1981), herein incorporated by reference. Candidate antigenic sites are screened experimentally to select those which generate antibodies that also recognize the pathogenic protein of interest and have optimal binding characteristics and minimal cross reactivity. This screening is considered routine experimentation by those skilled in the art.

The enzyme portion of the complex may be any enzyme or molecule which, when reacted with a substrate, provides for the detection of an antibody-antigen reaction. For example, the enzyme may be selected from the group consisting of alkaline phosphatase, horseradish peroxidase, beta-galactosidase, beta-glucuronidase, luciferase, and urease. Preferably, the enzyme used in the invention is alkaline phosphatase.

For binding sites containing a mAb bound to the ligand, the detection of antibody-antigen reactions may also be achieved using reporter molecules other than enzymes as the enzyme portion of the ligand-enzyme complex. For example, a modification of the recently developed electrochemiluminescence (ECL) technology (available from IGEN, Gaithersburg, Md.) may be used in the present invention, by replacing the enzyme portion of the ligand-enzyme complex with a ruthenium-labeled molecule. The resulting complex will be referred to as a ligand-reporter complex. Applying a low voltage to an electrode positioned near the binding site oxidizes the ruthenium label and its substrate, tripropylamine (TPA), to form strong oxidant and reductant compounds, respectively, which then react to form an excited state of the ruthenium label which decays to its starting ground state while releasing a photon at 620 nm. (See, e.g., Michael Carlowicz, "Electrochemiluminescence Could Spark an Assay Revolution", Clin. Lab. News, Vol. 21, p. 1–2 (August 1995), herein incorporated by reference.) The photon emissions are detected using a photo multiplier tube (PMT). The mAb is labeled with a quencher molecule capable of reducing detectable reporter activity, i.e., photon emissions, either by adsorbing light at 620 nm or by destabilizing the ruthenium compound when the quencher is located a short distance from the ligand-reporter complex. Thus, when the mAb is bound to the ligand-reporter complex, the amount of detectable emissions from the binding site is reduced, or suppressed, by the quencher molecule. Upon displacement from the complex of the mAb by a competing antigen or antibody, the amount of detectable emissions, or signal, increases.

Those skilled in the art will recognize that other reporter-quencher dye systems may be used in a manner similar to the above-described modification of ECL, wherein the reporter portion of the ligand-reporter complex comprises a molecule labeled with the reporter dye and the mAb is labeled with a quencher dye. For example, the reporter dye may be fluorescein and the quencher dye may be rhodamine. In embodiments where the signal is produced by a reporter molecule other than a classical enzyme, the term "enzyme's active site" means the reporter compound and "enzymatic activity" means detection of fluorescence.

The ligand-enzyme complex may be generated by chemically coupling the ligand to the enzyme near the enzymatic active site. Coupling reagents include, but are not limited to, sulfo-SMCC (Calbiochem, San Diego, Calif., Prod No.: 573115). For peptide ligands, the complex may also be constructed by inserting a DNA fragment coding for the peptide sequence, in frame, into the cloned gene for the enzyme such that the resulting expressed hybrid protein expresses the peptide positioned close to the enzymatic active site. Ruthenium-labelled molecules may be prepared using ORIGEN® TAG-NHS ester (IGEN, Inc.), which is a salt of ruthenium (II) tris(bipyridyl) chelate, a water soluble compound that is chemically modified on one of the bipyridyl ligands to enable labeling of proteins, haptens, and nucleic acids.

Figure 1:
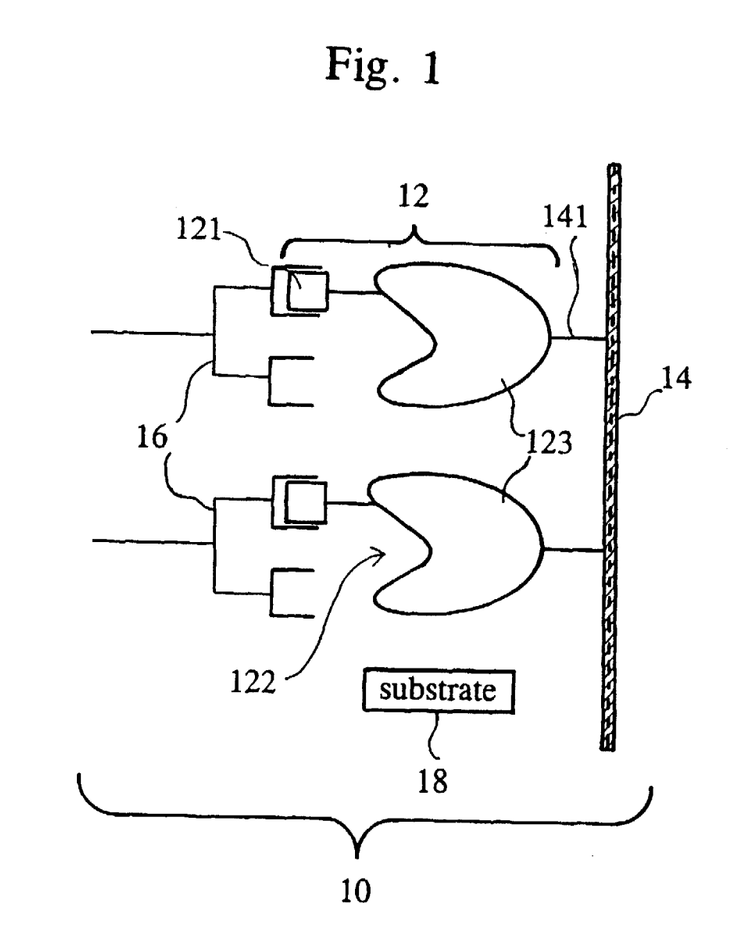
FIG. 1 is a schematic representation of a binding site in the preferred embodiment of the invention, showing two identical ligand-enzyme complexes attached to a solid support via a linker and a monoclonal antibody bound to the peptide ligand of each complex, thereby blocking substrate access to the enzyme's active site.
Figure 2:
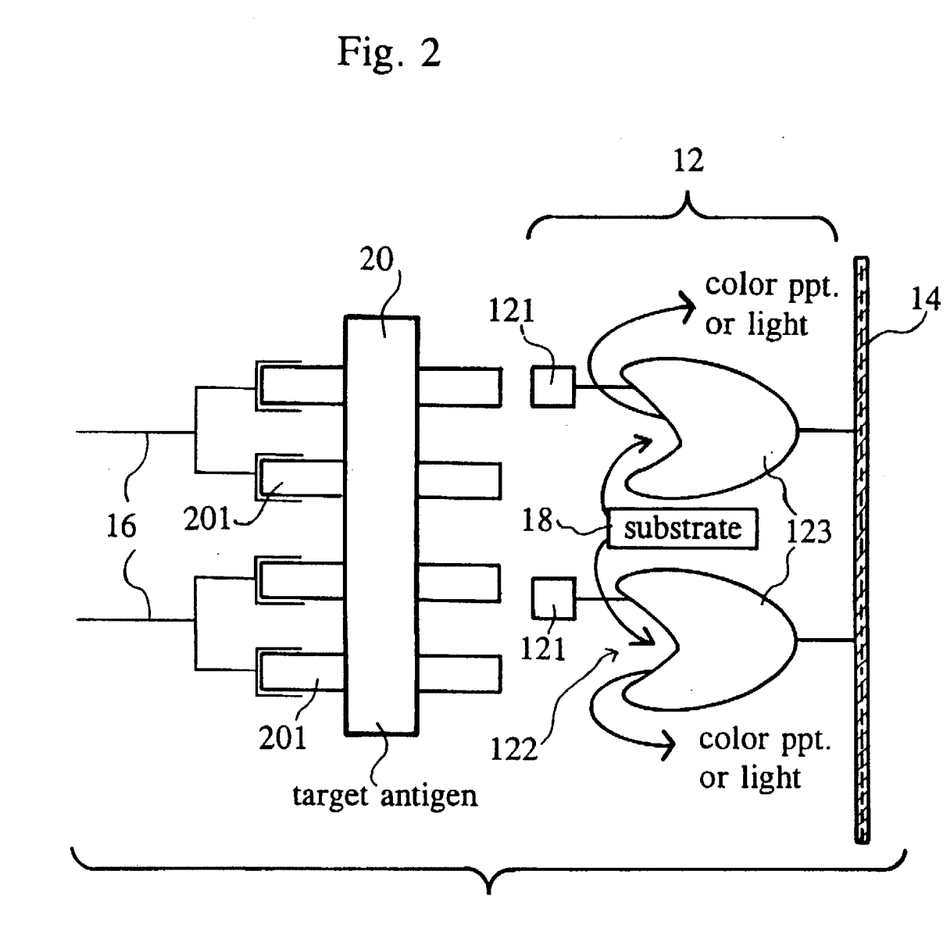
FIG. 2 is a schematic representation of antigen detection by the binding site of FIG. 1, showing the competitive release of the enzyme-inhibiting monoclonal antibody from the ligand-enzyme complexes in the presence of a target antigen from a pathogen, thereby allowing substrate access to the enzyme's active site.

Once the ligand-enzyme complex is generated, it is attached to a solid support to form a binding site. The attachment may be either noncovalent, e.g., the complex binds to the solid support through adsorption, or covalent, e.g., the complex is chemically coupled to the solid support via a linker molecule. The support is selected from substrates such as glass or plastic beads, membranes, microplates, magnetic particles, latex particles, nitrocellulose particles, and glass or plastic strips. The binding site may comprise only one molecule of the complex. Preferably the binding site contains a plurality of molecules of the complex. A preferred embodiment of the binding site is illustrated in FIG. 1. The binding site 10 comprises two identical ligand-enzyme complexes 12 attached to a solid support 14 via a linker 141. The binding site 10 also has a mAb 16 bound to the ligand portion 121 of the complex 12 in such a manner that the mAb 16 at least partially blocks access of a substrate 18 to the enzyme's active site 122. The mAb 16 is capable of binding both to the ligand 121 and to the target molecule but has a greater binding affinity for the target molecule than for the ligand 121. Thus, as illustrated in FIG. 2, when the binding site shown in FIG. 1 is exposed to a substrate 18 for the enzyme portion 123 of the complex 12 and to a target molecule 20 (FIG. 2) with a specific binding site 201 for the mAb 16, the competing target molecule 20 displaces the mAb 16 from the ligand 121, thereby allowing the exposed enzymatic active site 122 to react with the substrate 18 to generate a color precipitate or light.

The term mAb is intended to include: monoclonal antibodies generated using cells obtained from mice immunized with the ligand, the ligand conjugated to a carrier molecule, or the target molecule; monoclonal antibodies obtained by screening microorganisms genetically engineered to express the H- and L-chain repertoires of a particular species; monoclonal antibodies expressed by recombinant phage in which the expressed mAbs have been engineered to have desirable characteristics such as improved relative affinities for the target molecule and ligand or an improved ability to block the enzymatic active site; fragments of the aforesaid ligand or an improved ability to block the enzymatic active site; fragments of the aforesaid monoclonal antibodies, e.g., (Fab)$_2$ fragments; and monovalent antibodies. The term mAb also includes any proteinaceous or nucleic acid molecule engineered to be capable of blocking the enzyme's active site while binding to the ligand and having a higher binding affinity for the target antigen or antibody. To construct a binding site of the preferred embodiment, a solid support containing the immobilized ligand-enzyme complex is treated to prevent nonspecific adsorption of antibody using methods known in the art and then the mAb is allowed to bind to the complex.

After the binding site is constructed, its binding and enzymatic activities are assayed to determine if they are suitable for detecting the presence of the corresponding target molecule in a solution. For a binding site without mAb, the site has a suitable binding activity if the ligand portion of the immobilized ligand-enzyme complex can specifically capture the target molecule from the solution presented to the binding site. A binding site containing mAb bound to the ligand has a suitable binding activity if the mAb is released from the immobilized complex when, and only when, a competing target molecule is present in the solution.

The binding site is deemed to have a suitable enzymatic activity if there is a detectable change in the amount of signal produced by reaction of the enzyme portion of the complex with a substrate for the enzyme after a solution containing the corresponding target molecule is presented to the binding site. Thus, a binding site without bound mAb will have suitable enzymatic activity if the amount of signal is detectably reduced upon binding of the target molecule to the ligand. Alternatively, for a binding site containing bound mAb, a suitable enzymatic activity is defined as that providing a detectable increase in the amount of signal upon release of the mAb. In either embodiment, the enzymatic activity of the immobilized ligand-enzyme complex is preferably about 50%, and most preferably, at least 75%, of the activity of the unmodified enzyme, and binding of the cognate target molecule or mAb to the ligand preferably reduces this activity by 50%, and most preferably by at least 75%.

The substrate used to assay the binding and enzymatic activities of the ligand-enzyme complex may be any compound that reacts with the enzyme portion of the complex to produce a signal. Preferably, the substrate will produce a nonisotopic signal. For example, light emitting substrates contemplated by the invention include 1,2 dioxetane chemiluminescent substrates for complexes containing alkaline phosphatase, horseradish peroxidase, β-galactosidase, and β-glucuronidase (available from Tropix, Bedford, Mass.), luciferin for luciferase containing complexes, and TPA for ruthenium-labelled complexes. If a colorimetric signal is desired, substrates usable in the invention include 5-bromo-4-chloro-3-indolyl phosphate (BCIP) in combination with nitro blue triazolium (NBT) for complexes containing alkaline phosphatase, o-nitrophenyl-β-galactopyranoside (ONPG) for β-galactosidase, and 4-chloro-1-napthol for horseradish peroxidase. In addition, a change in the pH of the reaction medium is a detectable signal which may be produced by using urea as the substrate and urease as the enzyme.

Once operable binding sites for different target molecules are constructed, at least two binding sites for different target molecules are arranged in a known relationship to allow simultaneous detection of multiple antigens or antibodies in a sample. The nature of this arrangement is such that the sample may be presented to the binding sites in a single operation to provide essentially simultaneous contact of the sample with the different binding sites. Furthermore, the arrangement must allow the different binding sites to be distinguishable from each other.

For example, the binding sites may be arranged on the surface of a membrane and the sample applied to the membrane or strip by the single operation of spraying the membrane with the sample or dipping the membrane into the sample. Preferably, the binding site comprises a ligand-enzyme complex attached to a bead and the different binding sites, i.e., different beads, are arranged along the length of a tube. In this embodiment, simultaneous contact of the sample with the binding sites is achieved by the single operation of flowing the sample from one end of the tube to the other end. For example, the tube may be held in a vertical or horizontal position and the sample presented to the binding sites by the single operation of applying the sample to one end of the column such that it moves across the column or by the single operation of applying suction to one of the column to draw the sample into the column from its other end.

The ligand-enzyme complexes in the different binding sites may be derived from the same enzyme or different enzymes. Preferably, each binding site contains ligand-enzyme complexes derived from the same enzyme to allow the use of a single substrate during the immunoassay.

In one embodiment of the invention, a sample is tested for the presence of multiple target antigens or antibodies by first applying a substrate for the enzyme to at least two binding sites for different known target molecules to determine the amount of enzymatic activity of each binding site in the absence of any target molecule (background level). The amount of activity in each site is quantifiable by the amount of a signal produced upon reaction of the substrate with the enzyme and is directly related to the ability of the substrate to interact with the enzyme's active site. This amount of signal produced by each binding site is referred to as the control value for that site.

After the control values are determined, an optional washing step is performed in which the binding sites are washed with a buffer solution until the binding sites no longer generate a signal. Then the sample is presented to the binding sites, along with fresh substrate if the optional washing step was done, and the binding sites assayed for enzymatic activity. A change in the amount of signal produced by a specific binding site as compared to the control value for that site indicates that the corresponding target molecule is present in the sample. For example, in a competitive binding assay where a mAb blocks the enzymatic activity or reporter molecule from being active, the control value of the assay will be less than the amount of signal produced when the target molecule is present due to the removal of the mAb blocking or sequestering the site by the target molecule. In a direct binding assay, the control value would give a strong signal and the presence of a particular antigen or antibody would reduce the signal measured thereby indicating the presence of the target being measured. Therefore, the control value is simply a measurement of the assay system in the absence of the target, the presence of which causes a change that can be measured or determined.

Additionally, a negative control site can be incorporated that consists of a bound mAb to a unique peptide ligand, i.e., a peptide not found anywhere in nature, in such a way that the reaction of the enzyme with its substrate is inhibited. The signal from the negative control site should remain about the same after presenting the sample. An increase in signal from the negative control site would indicate that a nonspecific denaturant in the sample has caused displacement of the mAb from the negative control site and, by extrapolation, that denaturing of binding sites for target molecules may have occurred, leading to the detection of false positives.

Preferably, the invention further comprises presenting the sample mixed with substrate to a positive control binding site to verify the ability of the substrate to generate a signal and the operability of the signal detector. The positive control site may comprise a nonmodified enzyme (no attached ligand) attached to a solid support. Preferably, the positive control binding site may comprise a specific binding site for a target molecule added to the sample. The invention also provides a detection device for rapidly testing a sample for the presence of multiple antigens or antibodies comprising at least two of the above described binding sites arranged in a known order with respect to each other. The shape, size and relative positions of the binding sites are a matter of design choice and will depend somewhat upon the support chosen to immobilize the ligand-enzyme complexes.

Figure 3:
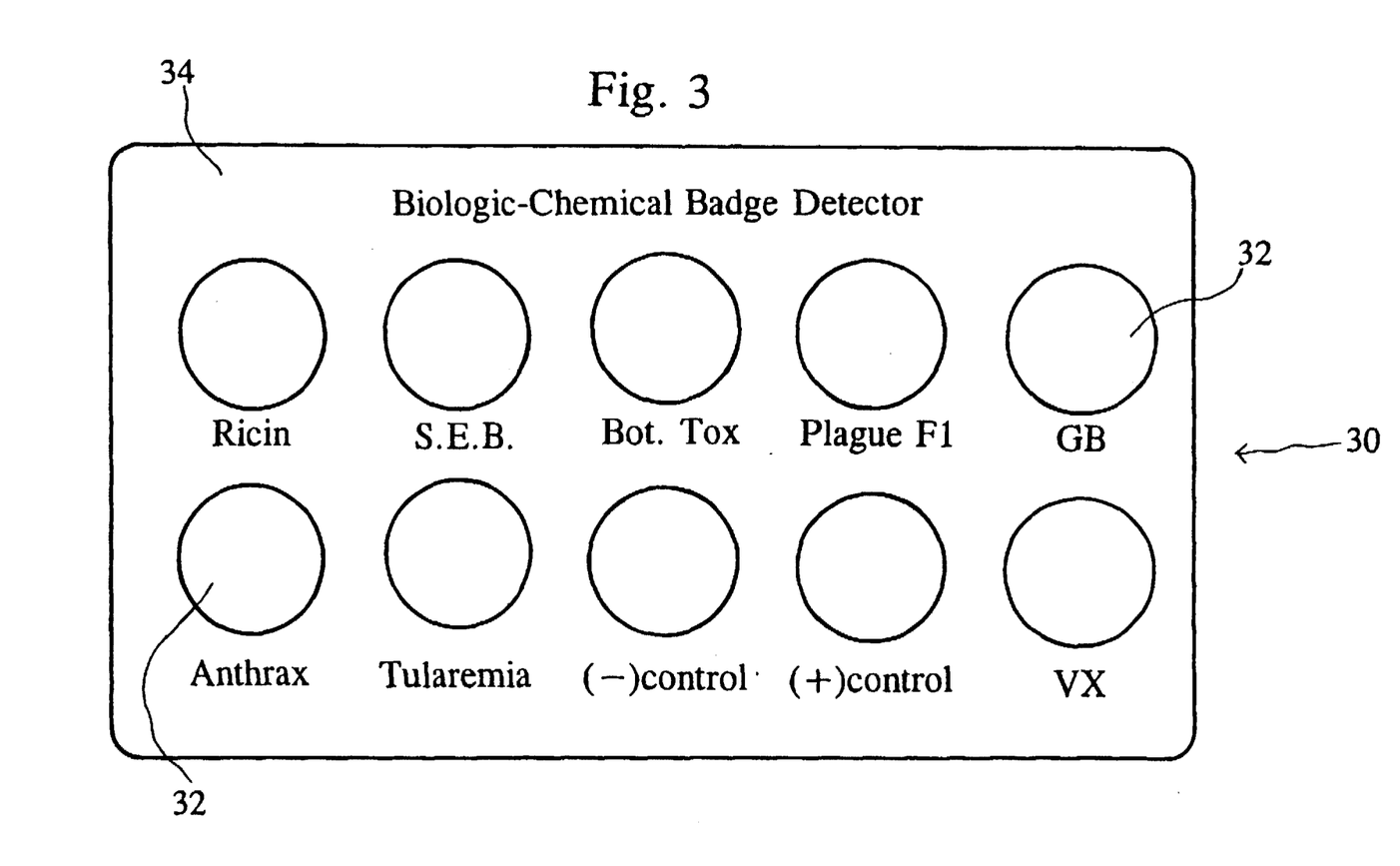
FIG. 3 is a schematic representation of a device according to the invention, showing a badge detector with binding sites contained in separate circular detection zones specific for the following pathogens: ricin toxin, staph enterotoxin B (S.E.B.), botulinum A toxin (Bot. Tox.), plague F1, the nerve agents GB ($(CH_3PCO)(COR)F$, wherein R is $iC\ H_3)_7$ and VX ($(CH_3P(O)(OC_2H_5)SR_2$, wherein $R_2$ is $CH_2CH_2N$ $(iC_3H_7)_2$), anthrax, and tularemia.

A device according to the invention is illustrated in FIG. 3. The Biologic-Chemical Badge Detector 30 has ten discrete binding sites 32 arranged on a membrane support 34. Eight of the binding sites are specific for the designated pathogens; the other two sites are controls. Similar badge detectors may be constructed using a plastic strip as the support, or using a microtitre plate having the different ligand-enzyme complexes immobilized in separate wells.

The invention also contemplates badge detectors similar to that shown in FIG. 3 wherein the substrate is preapplied to the binding sites and retained by various means until the badge detector is used. Such detectors containing a preapplied calorimetric substrate are particularly suited to detecting multiple target molecules in the field. The substrate is retained, for instance, by a layer of a gelatinous material spread over the binding sites or by a plastic film having an adhesive backing placed over the binding sites. The gelatinous material or plastic film can be removed before the badge detector is exposed to pathogens, i.e., just prior to entering a suspected chemical agent attack site, or just prior to entry into combat, etc.

In a preferred embodiment, the different binding sites of the detection device comprise beads to which different ligand-enzyme complexes are attached and the different binding sites are placed in a known order in a tube. Preferably, the different binding sites are separated from each other by empty beads, i.e., lacking ligand-enzyme complexes. Thus, if a plurality of beads is used in each binding site, the different binding sites will have the shape of bands along the tube. The tube may be transparent to allow visual detection of a color change or detection of light emission with one or more luminometers disposed outside the tube. For example, a single luminometer may be moved the length of the tube stopping at the location of each binding site to monitor for light emission from that site, or multiple luminometer detectors may be positioned next to the location of each binding site. Alternatively, the tube is nontransparent and is provided with means for detecting light emission from the banded detection zones, e.g., by a plurality of miniature luminometers attached to the interior wall of the tube at positions corresponding to the location of each detection zone. The tube may also comprise a solution containing the substrate dispersed throughout the column, the substrate solution retained in the column by stoppers capping the top and bottom of the tube. In a preferred embodiment, the detector comprises a plurality of identical tubes for simultaneously testing multiple samples for the presence of multiple target antigens or antibodies.

Figure 4:
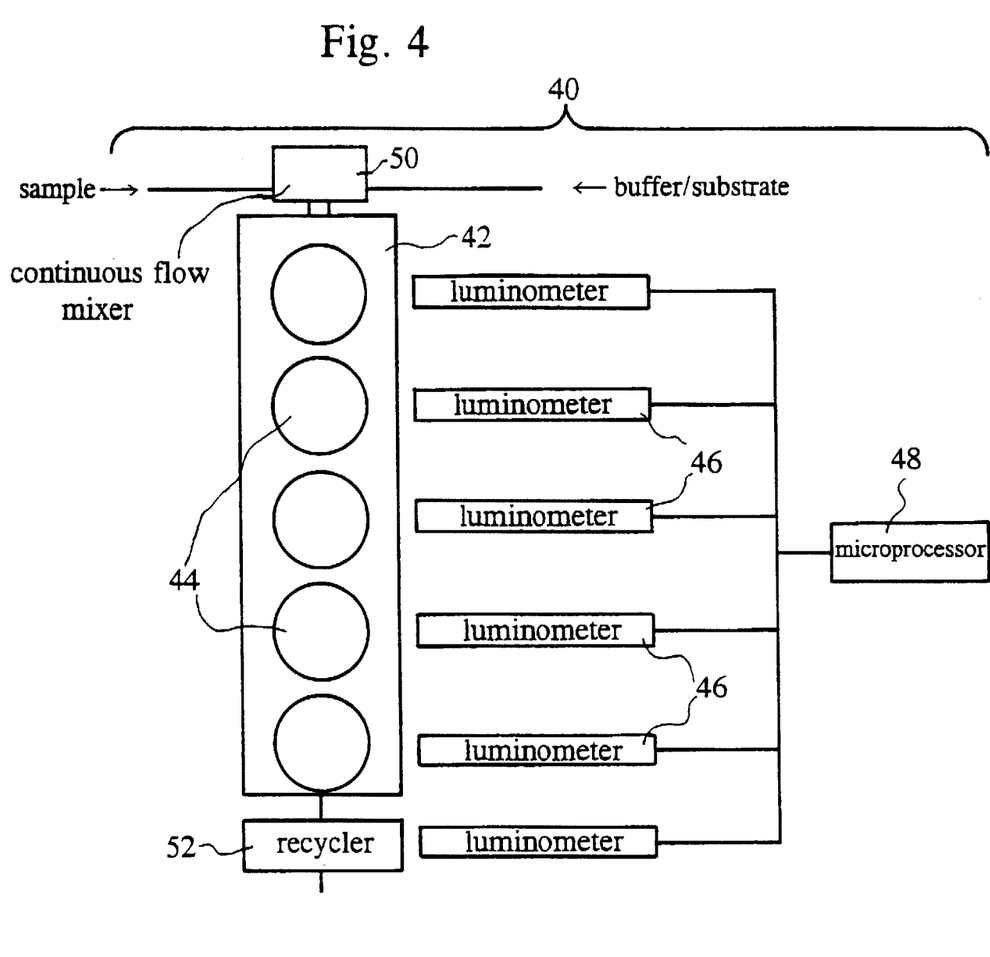
FIG. 4 is a schematic representation of a detection system according to the invention, showing a tube detector having binding sites contained in separate detection zones arranged within a capillary tube, luminometer detectors for monitoring enzymatic activity in each of the zones which are linked to a microprocessor, and a recycling system for capturing and recycling of the released monoclonal antibodies.

Tube embodiments of a detector device may be incorporated into an integrated detection system as illustrated in FIG. 4. This system 40 includes a transparent capillary tube 42 containing several different binding sites 44, and multiple luminometers 46 disposed next to each of the binding sites for detecting light emitted from the binding sites. Each luminometer 46 is operably connected to a microprocessor 48 which has an analyzer for analyzing the light signals detected by the luminometers 46 and a reporter for reporting whether specific antigens or antibodies were detected in the sample. This report may be visual, i.e., such as lights that turn on when one or more specific target antigens or antibodies are detected, or a printout which lists the antigens or antibodies detected. Alternatively, or in addition to a visual report, the report may include an audible alarm which is activated when one or more target antigens or antibodies are detected. The system also comprises a continuous flow mixer 50 which has means for mixing the sample and substrate and means for applying the mixture to the tube and a recycler 52 for recycling any mAbs released from the binding sites by their binding to target molecules.

The invention may be further understood by reference to the nonlimiting example set forth below.

EXAMPLE—DETECTION OF MULTIPLE PATHOGENS

Antibody Generation—Antigenic sites of the envelope proteins of three hemorrhagic viruses, Ebola virus, Hanta virus, and Lassa virus are determined using the Hopp and Woods hydrophobicity computer program. The following synthetic peptides, which contain an amino acid sequence corresponding to a selected antigenic site for each of the viruses with a cysteine residue added to the carboxy terminus for coupling the peptide to a carrier molecule, are manufactured.

Ebola: Asp-Lys-Thr-Leu-Pro-Asp-Gln-Gly-Asp-Asn-Asp-Cys (SEQ ID NO:1);

Hanta: Leu-Arg-Lys-Ile-Lys-Glu-Glu-Phe-Glu-Lys-Thr-Lys-Gly-Cys (SEQ ID NO:2);

Lassa: Gln-Arg-Thr-Arg-Asp-Ile-Tyr-Ile-Ser-Arg-Arg-Leu-Leu-Gly-Cys (SEQ ID NO:3);

These peptides are coupled to a carrier molecule such as tetanus toxoid using sulfo-SMCC (Calbiochem, San Diego, Calif., Prod No.:573115). The carrier-coupled peptides are then used to immunize mice, and monoclonal antibodies are prepared substantially as described by Harlow in *Antibodies*, Cold Spring Harbor, ed. (1988), herein incorporated by reference. Selection of the most appropriate monoclonal antibody specific for each of the peptide antigenic sites is performed by screening for antibodies which inhibit a genetically engineered enzyme expressing the same epitope.

Making Ligand-Enzyme Complexes—Three alkaline phosphatase (AP) hybrid enzymes, each expressing one of the above viral-specific epitopes at a position within the enzyme such that a monoclonal antibody binding to the epitope interferes with the enzymatic site of alkaline phosphatase, are prepared as follows. First, the alkaline phosphatase gene encoded by *E. coli* (phoA) is cloned into a plasmid containing the f1 recognition site of bacteriophage m13. Then, suitable cloning sites are introduced into the cloned phoA gene near amino acids 407–408 using site directed mutagenesis performed substantially as described by Sambrook in *Molecular Cloning*, Cold Spring Harbor, ed. (1989), herein incorporated by reference. In particular, KpnI and ScaII restriction sites are introduced into the phoA gene after amino acid 407 by hybridizing to the cloned phoA gene an oligonucleotide having the sequence:

5'-GGCAACACGGTGGTACCAGTCACCGCGGATCACGCCC-3' (SEQ ID NO:4).

Following primer extension of the oligonucleotide and transfection of competent prokaryotic cells, clones are selected which contain the new KpnI and ScaII restriction sites in the phoA gene.

The modified phoA gene is then subcloned into one of the pMAL-2 expression vectors of the Protein Fusion and Purification System marketed by New England Biolabs (Beverly, Mass.). Since the pMAL-2 vectors do not contain KpnI or SacII sites, the resulting phoA-pMAL plasmid may be cleaved at the desired site within the phoA gene by digestion with KpnI and SacII.

Oligonucleotide linkers encoding the viral specific epitopes listed above in SEQ ID NOS: 1–3, minus the carboxy terminal cysteine residue and containing appropriate Kpn and SacII linker sequences, are prepared from hybridizing oligonucleotide pairs having the following sequences:

Ebola Virus Linker
5'-CGATAAAACGCTTCCCGATCAAGGCGATAACGATACCGC-3' (SEQ ID NO:5)
3'-CATGGCTATTTTGCGAAGGGCTAGTTCCGCTATTGCTATGG-5' (SEQ ID NO:6)

Hanta Virus Linker
5'-CCTCCGCAAAATTAAAGAAGAATTTGAAAAAACCAAAGGCACCGC-3' (SEQ ID NO:7)
3'-CATGGGAGGCGTTTTAATTTCTTCTTAACTTTTTTGGTTTCCGTGG-5' (SEQ ID NO:8)

Lassa Virus Linker
5'-CCAACGCACCCGCGACATTTATATTTCTCGCCGCCTCCTCGGCACCGC-3' (SEQ ID NO:9)
3'-CATGGGTTGCGTGGGCGCTGTAAATATAAAGAGCGGCGGAGGAGCCGTGG-5' (SEQIDNO:10).

These linkers are separately inserted into the Kpn I and SacII sites of the phoA-pMAL plasmid to form recombinant plasmids coding for three different peptide-AP complexes. Each of the recombinant plasmids is transfected into *E. coli* and induced to express a maltose binding protein (MBP)—peptide-AP fusion protein at high levels. The fusion protein is purified from other proteins produced by the transformed cells by capturing the fusion protein out of the protein mixture on an amylose column followed by eluting the fusion protein with maltose. Each peptide-AP complex is cleaved from its respective fusion protein with the specific protease factor Xa and separated from the liberated MBP by passing the mixture over an amylose column.

The isolated peptide-AP complexes are assayed for enzyme activity and used to screen for monoclonal antibodies that lower the enzyme activity of only the modified enzymes and not that of unaltered alkaline phosphatase. These peptide-specific antibodies (i.e., do not exhibit non-specific binding to unaltered AP) are then further screened to select monoclonal antibodies suitable for use in the invention by introducing the competing viral protein antigens onto ELISA plates containing the inhibiting monoclonal antibodies bound to the peptide-AP complexes. Suitable monoclonal antibodies are those peptide-specific antibodies which are displaced from the peptide-AP complexes via their stronger binding affinity for the corresponding native viral protein antigens. Monoclonal cell lines producing suitable antibodies are expanded and the antibodies are purified from the cell cultures using affinity chromatography and protein A/G columns.

Once a suitable combination of mAb and peptide-AP complex is generated for each of the three viruses of interest, binding sites for the viruses are constructed. First, the peptide-AP complexes are coupled to different batches of uniform beads either by adsorption or by chemical coupling. Each binding site, i.e., batch of beads, is then treated to block non-specific absorption using a solution of bovine serum albumin followed by washing in PBS/0.01% tween-20. A portion of each batch of treated beads is reserved and the remainder mixed with the mAb for the viral antigen to bind the mAb to its corresponding peptide-AP complex on the treated beads to form a viral specific binding site. Unbound mAb is removed from the beads by washing extensively in PBS/0.01% tween-20. Each binding site is then assayed to determine if it has suitable binding and enzymatic activities by comparing the chemiluminescent output of the reserved portion of beads (i.e., no mAb) mixed with substrate to the output of the binding site (i.e., has bound mAb).

Viral-specific binding sites having suitable binding and enzymatic activities, and positive and control sites, are then arranged in a known order in a transparent tube, separated from each other by empty beads. The operation of the detector device is validated by applying to the tube a chemiluminescent substrate for alkaline phosphate and measuring light emissions from each binding site to determine the control value for each of the binding sites. After extensive washing with a buffer solution, a series of test samples containing one or more of the three viruses of interest are applied to the tube along with the substrate. The light emissions from the viral-specific binding sites are compared to the control value. A higher amount of light emitting from a viral-specific site relative to the control value indicates that the sample contains the corresponding virus.

Those skilled in the art will understand that a negative control is not needed to carry out the invention, however, a negative control would serve as an indicator of the condition of the column since a change in the signal measured may indicate column failure. For example, the presence of a target molecule in a sample can be detected by measuring the light emitted from the binding sites exposed to the substrate both before and after applying the sample. An increase in emitted light, for a binding site containing bound mAb, or a decrease in emitted light, for a binding site without bound mAb, indicates the presence of the corresponding target antigen or antibody, whereas the detection of altered activity in a negative control site would indicate a false positive signal or loss of column sensitivity depending upon the assay.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: internal     ( v i ) ORIGINAL SOURCE:
        ( A ) ORGANISM: Ebola virus     ( i x ) FEATURE:
        ( A ) NAME/KEY: Binding-site
        ( B ) LOCATION: 1..12

( x i ) SEQUENCE DESCRIPTION: SEQ ID NO:1:

```
Asp Lys Thr Leu Pro Asp Gln Gly Asp Asn Asp Cys
1               5                   10
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: internal     ( v i ) ORIGINAL SOURCE:
        ( A ) ORGANISM: HANTA VIRUS     ( i x ) FEATURE:
        ( A ) NAME/KEY: Binding-site
        ( B ) LOCATION: 1..14

( x i ) SEQUENCE DESCRIPTION: SEQ ID NO:2:

```
Leu Arg Lys Ile Lys Glu Glu Phe Glu Lys Thr Lys Gly Cys
1               5                   10
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear     ( i i ) MOLECULE TYPE: peptide     ( i i i ) HYPOTHETICAL: NO     ( i v ) ANTI-SENSE: NO     ( v ) FRAGMENT TYPE: internal     ( v i ) ORIGINAL SOURCE:
        ( A ) ORGANISM: Lassa virus     ( i x ) FEATURE:
        ( A ) NAME/KEY: Binding-site
        ( B ) LOCATION: 1..15

( x i ) SEQUENCE DESCRIPTION: SEQ ID NO:3:

```
Gln  Arg  Thr  Arg  Asp  Ile  Tyr  Ile  Ser  Arg  Arg  Leu  Leu  Gly  Cys
1                  5                        10                           15
```

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "OLIGODEOXYNUCLEOTIDE"

( i i i ) HYPOTHETICAL: NO

( i v ) ANTI-SENSE: NO

( x i ) SEQUENCE DESCRIPTION: SEQ ID NO:4:

```
GGCAACACGG TGGTACCAGT CACCGCGGAT CACGCCC                                    37
```

( 2 ) INFORMATION FOR SEQ ID NO:5:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "LINKER"

( i i i ) HYPOTHETICAL: YES

( i v ) ANTI-SENSE: NO

( v i ) ORIGINAL SOURCE:
        ( A ) ORGANISM: Ebola virus     ( x i ) SEQUENCE DESCRIPTION: SEQ ID NO:5:

```
CGATAAAACG CTTCCCGATC AAGGCGATAA CGATACCGC                                  39
```

( 2 ) INFORMATION FOR SEQ ID NO:6:

( i ) SEQUENCE CHARACTERISTICS:
        ( A ) LENGTH: 41 base pairs
        ( B ) TYPE: nucleic acid
        ( C ) STRANDEDNESS: single ( D ) TOPOLOGY: linear ( i i ) MOLECULE TYPE: other nucleic acid
        ( A ) DESCRIPTION: /desc = "oligodeoxynucleotide"

( i i i ) HYPOTHETICAL: YES ( i v ) ANTI-SENSE: NO ( v i ) ORIGINAL SOURCE:
        ( A ) ORGANISM: Ebola virus ( x i ) SEQUENCE DESCRIPTION: SEQ ID NO:6:

CATGGCTATT TTGCGAAGGG CTAGTTCCGC TATTGCTATG G         41

( 2 ) INFORMATION FOR SEQ ID NO:7:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligodeoxynucleotide"

( i i i ) HYPOTHETICAL: YES ( i v ) ANTI-SENSE: NO ( v i ) ORIGINAL SOURCE:
        ( A ) ORGANISM: Hanta virus ( x i ) SEQUENCE DESCRIPTION: SEQ ID NO:7:

CCTCCGCAAA ATTAAAGAAG AATTGAAAA AACCAAGGC ACCGC         45

( 2 ) INFORMATION FOR SEQ ID NO:8:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligodeoxynucleotide"

( i i i ) HYPOTHETICAL: YES ( i v ) ANTI-SENSE: NO ( v i ) ORIGINAL SOURCE:
        ( A ) ORGANISM: Hanta virus ( x i ) SEQUENCE DESCRIPTION: SEQ ID NO:8:

CATGGGAGGC GTTTAATTT CTTCTTAACT TTTTGGTTT CCGTGG         46

( 2 ) INFORMATION FOR SEQ ID NO:9:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGODEOXYNUCLEOTIDE"

( i i i ) HYPOTHETICAL: YES ( i v ) ANTI-SENSE: NO ( v i ) ORIGINAL SOURCE:
        ( A ) ORGANISM: Lassa virus ( x i ) SEQUENCE DESCRIPTION: SEQ ID NO:9:

CCAACGCACC CGCGACATTT ATATTTCTCG CCGCCTCCTC GGCACCGC            48

( 2 ) INFORMATION FOR SEQ ID NO:10:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "OLIGODEOXYNUCLEOTIDE"

( i i i ) HYPOTHETICAL: YES

( i v ) ANTI-SENSE: NO

( v i ) ORIGINAL SOURCE:
        ( A ) ORGANISM: Lassa virus     ( x i ) SEQUENCE DESCRIPTION: SEQ ID NO:10:

CATGGGTTGC GTGGGCGCTG TAAATATAA

16. The device of claim 15, wherein the ligand comprises a binding partner of the target antigen or antibody.

17. The device of claim 15, wherein the ligand comprises a nucleic acid or oligonucleotide.

18. The device of claim 15, wherein at least one of said known binding sites further comprises a mAb bound to the ligand and at least partially blocking the active site of the enzyme, wherein said mAb has a greater binding affinity for the target antigen or antibody than for the ligand.

19. The device of claim 15, wherein at least one of said known binding sites comprises a plurality of molecules of the ligand-enzyme complex.

20. The device of claim 15, further comprising a positive control binding site and a negative control binding site.

21. The device of claim 20, wherein the support is selected from the group consisting of glass beads, plastic beads, magnetic particles, nitrocellulose particles and latex particles, and the binding sites are arranged in a known order in a tube.

22. The device of claim 21, wherein the tube is provided with a plurality of luminometers, said luminometers being disposed in the vicinity of the binding sites and operably linked to a microprocessor having means for analyzing information received from the binding sites and means for reporting detection of target antigens or antibodies in the sample.

23. The device of claim 15, wherein the enzyme is selected from the group consisting of alkaline phosphatase, horseradish peroxidase, beta-galactosidase, beta-glucuronidase, luciferase, and urease.

24. The device of claim 23, wherein the enzyme is alkaline phosphatase.

25. The device of claim 18, wherein the enzyme is a molecule labeled with a reporter compound and the mAb is a molecule labeled with a quencher compound.

26. The device of claim 25, wherein the reporter compound is ruthenium (II) tris(bipyridyl) chelate and the quencher compound adsorbs light at 620 nm.

27. The device of claim 18, wherein the ligand comprises a peptide derived from an antigenic site of the target antigen or antibody.

28. The device of claim 27, wherein the known binding sites are specific for target molecules of biologic origen.

29. The device of claim 28, wherein the target molecules are selected from the group consisting of ebola virus, hanta virus, and lassa virus.

30. The device of claim 15, wherein the support is selected from a membrane and a plastic strip.

31. The device of claim 30, wherein the support is provided with a substrate for the enzyme and means for retaining the enzyme until the device is exposed to the sample.

* * * * *